United States Patent
Ghareh Baghi et al.

(10) Patent No.: US 11,925,413 B2
(45) Date of Patent: Mar. 12, 2024

(54) DETERMINING OPHTHALMIC PARAMETERS

(71) Applicant: Arash Ghareh Baghi, Västerås (SE)

(72) Inventors: Arash Ghareh Baghi, Västerås (SE); Mozaffar Yousefi, Tehran (IR); Mehdi Salehi, Tehran (IR)

(73) Assignee: Arash Ghareh Baghi, Västerås (SE)

( * ) Notice: Subject to any disclaimer, the term of this patent is extended or adjusted under 35 U.S.C. 154(b) by 0 days.

(21) Appl. No.: 18/253,277

(22) PCT Filed: Nov. 23, 2021

(86) PCT No.: PCT/SE2021/051163
§ 371 (c)(1),
(2) Date: May 17, 2023

(87) PCT Pub. No.: WO2022/115020
PCT Pub. Date: Jun. 2, 2022

(65) Prior Publication Data
US 2023/0346213 A1    Nov. 2, 2023

(30) Foreign Application Priority Data
Nov. 25, 2020    (SE) .................... 2051370-1

(51) Int. Cl.
*A61B 3/10*    (2006.01)
*A61B 3/16*    (2006.01)

(52) U.S. Cl.
CPC .............. *A61B 3/1005* (2013.01); *A61B 3/16* (2013.01)

(58) Field of Classification Search
CPC ................................ A61B 3/1005; A61B 3/16
USPC .......................................................... 351/205
See application file for complete search history.

(56) References Cited

U.S. PATENT DOCUMENTS

| 6,093,147 A | 7/2000 | Kontiola | |
| 7,761,139 B2* | 7/2010 | Tearney | A61B 5/6848 |
| | | | 600/476 |
| 2017/0245751 A1* | 8/2017 | Dubois | A61B 5/0295 |
| 2018/0368681 A1 | 12/2018 | Makkeli et al. | |
| 2019/0380577 A1* | 12/2019 | Martin | A61B 3/0025 |
| 2023/0076641 A1* | 3/2023 | McCafferty | A61B 8/4455 |

FOREIGN PATENT DOCUMENTS

| CN | 104274153 A | 1/2015 |
| WO | WO 2017/208131 A1 | 12/2017 |

OTHER PUBLICATIONS

De Padua Soares Bezerra, Bernardo, et al., "Intraocular pressure measurement after corneal transplantation," Survey Of Ophthalmology, Mar. 5, 2019, pp. 639-646, vol. 64, No. 5, Elsevier, Inc., US.
International Searching Authority, International Search Report and Written Opinion received for International Application No. PCT/SE2021/051163, dated Feb. 1, 2022, 13 pages, European Patent Office, NL.

* cited by examiner

*Primary Examiner* — Mohammed A Hasan
(74) *Attorney, Agent, or Firm* — Alston & Bird LLP (57) ABSTRACT

A computer-implemented method, a computer program, a system and a method for analyzing a time-velocity curve and calculating based on the time-velocity curve ophthalmic parameters.

15 Claims, 4 Drawing Sheets

DETERMINING OPHTHALMIC PARAMETERS

CROSS REFERENCE TO RELATED APPLICATIONS

This application is a National Stage Application, filed under 35 U.S.C. 371, of International Application No. PCT/SE2021/051163, filed Nov. 23, 2021, which international application claims priority to and the benefit of Swedish Application No. 2051370-1, filed Nov. 25, 2020; the contents of both of which are hereby incorporated by reference in their entirety.

TECHNICAL FIELD

The present disclosure is related to a computer-implemented method, a computer program, a system and method for determining ophthalmic parameters, such as intraocular pressure, cornea thickness, tear film thickness and corrected intraocular pressure.

BACKGROUND ART

The cornea is the outmost, transparent layer of the eye and plays an important role in human vision. It makes up about 70% of the optical power of the eye, especially the centre part thereof where light passes through towards the retina. The thickness of the central part of the cornea, Central Corneal Thickness (CCT), is the most important factor in corneal stability. The thickness of the CCT is averagely 530±10 µm in humans, and varies from 300 to 1500 µm in animals, depending on the type of animal. This thickness value is employed by ophthalmologists, not only in the clinical routines as a diagnostic parameter for diseases like glaucoma, but also as a procedural pre-operatory parameter for surgical operations, such as refractive surgeries and corneal transplantation.

In healthy eyes, the cornea is covered by a thin layer of a viscous liquid, a tear film. The tear film is approximately 5 µm and covers the outer mucosal surface of eyes. The tear film creates an interface between the ocular surface and the surrounding environment. If the thickness of the tear film is thinner, there is a condition called dry eye disease. Symptoms thereof may range from mild eye burning and itching to corneal perforation in severe cases.

Intraocular pressure of eye is the pressure created by the continual renewal of fluids within the eye, which is increased at the presence of disease such as glaucoma.

Glaucoma is a chronic, end-stage disease that can bring irreversible damage to the eyes if remained untreated. Patients with glaucoma lose their central vision gradually until there is a complete degeneration. A person with high intraocular pressure is at high risk of glaucoma. Timely diagnosis of the disease can effectively enhance the disease management, while late diagnosis on the other hand can cause permanent damages and requires a more complex treatment.

Intraocular pressure (IOP) is a diagnostic parameter of the eye that plays an effective role in the timely diagnosis of eye diseases such as glaucoma. Accurate measurement of intraocular pressure helps to improve the diagnosis of glaucoma patients.

By direct measurement of the IOP through the corneal interface, the CCT affects the measured value of the intraocular pressure. This is systematically ignored due to lack of a reliable technology for simultaneous measurement of CCT and IOP. As a result, a systematic error is often concomitant with IOP measurements. The IOP value may be defined in two ways: a) as an uncorrected IOP, and b) as a corrected IOP.

The uncorrected IOP is measured without taking into account the actual thickness of the cornea, using a fixed and pre-set reference value of the CCT, i.e. 530 µm. In for example US2018368681 A1 is described a device and method for measuring uncorrected IOP. Existing devices for measuring uncorrected IOP, although typically inexpensive, fail to provide sufficient accuracy, especially when measuring on an eye which has previously undergone refractive surgery and therefore has a thinner CCT than normal. The IOP inaccuracy is also a problem when measuring on different animals where the CCT spans a broad range.

Corrected intraocular pressure is a parameter that is used to unify the effects of central corneal thickness on intraocular pressure relative to a specific reference thickness. Corrected intraocular pressure is more accurate and more important than the uncorrected alternative, and requires more expensive and sophisticated equipment. With current technology, corneal thickness and uncorrected intraocular pressure are measured independently and thereafter the corrected IOP is calculated using the measured parameters. Each of the measurements require expensive devices.

Nowadays, due to the large demand of laser operations (surface ablation) such as LASIK (laser-assisted in situ keratomileusis), LASEK (Laser Assisted Sub-Epithelial Keratectomy), and PRK (photorefractive keratectomy), the corneal thickness is noticeably decreased in those individuals who underwent such the interventions. These individuals are prone to the risk of IOP under-estimation, and consequently glaucoma misdiagnosis, when the IOP is measured in an uncorrected way.

Hence, there is clearly a need for a way of measuring ophthalmic parameters, such as corrected intraocular pressure, which is simpler, faster and less expensive.

SUMMARY OF THE INVENTION

It is an object of the present disclosure to provide a computer-implemented method for determining ophthalmic parameters, the ophthalmic parameters including intraocular pressure, corneal thickness, tear film thickness and corrected intraocular pressure.

Further objects are to provide a computer program, a system and a method for calculating such ophthalmic parameters.

The invention is defined by the appended independent claims. Non-limiting embodiments emerge from the dependent claims, the appended drawings and the following description.

According to a first aspect there is provided a computer-implemented method for analysing a time-velocity curve, the time-velocity curve comprising registered velocity and time of a probe body during movement of the probe body in a first direction travelling towards a corneal outer surface of an eye of a subject, during impact of an end of the probe body with the corneal outer surface, when completely stopped on the eye, and during rebound movement of the probe body in a second direction, opposite to the first direction, the computer-implemented method comprising calculating an intraocular pressure of the eye as a slope in the time-velocity curve between a time when the end of the probe body first impacts the corneal outer surface and the time when the probe body is completely stopped on the eye, and calculating a central cornea thickness using a velocity of the probe body in the time-velocity curve at a moment of contact of the end of the probe body with the corneal outer surface, $V_r$, and a velocity of the probe body in the time-velocity curve at a moment when the probe body leaves the corneal outer surface during rebound movement of the probe body in the second direction, $V_b$.

When the probe body is completely stopped on the eye it has no speed in the first or second direction.

The central area of the corneal outer surface is here meant an area in the middle of the eye pupil. The central area could have a diameter of less than 2 mm.

A central cornea thickness is calculated from the speed-velocity curve using a velocity of the probe body at a moment of contact of the end of the probe with the corneal outer surface, $V_r$, and a velocity of the probe body at the moment when the end of the probe body leaves the corneal outer surface during rebound movement of the probe body in the second direction, $V_b$. For this calculation any nonlinear, linear or piece-wisely linear function of the time-velocity curve may be used.

The intraocular pressure obtained is the so called uncorrected intraocular pressure obtained without taking into account the actual thickness of the cornea. When calculating this pressure, the slope may be measured as an average slope using for example three evenly distributed points on the slope.

The uncorrected intraocular pressure may be a non-correct intraocular pressure if an eye has previously undergone refractive surgery and therefore has a thinner cornea thickness than normal. Further, the cornea thickness spans a broad range between different animals.

In the computer-implemented method the uncorrected intraocular pressure and the thickness of the central area of the cornea is calculated from the same time-velocity curve. The computer-implemented method may then use both these values to calculate a corrected intraocular pressure.

According to a second aspect there is provided a computer program comprising instructions which, when the program is executed by a computer, cause the computer to carry out analysis of a time-velocity curve, the time-velocity curve comprising registered velocity and time of a probe body during movement of the probe body in a first direction travelling towards a corneal outer surface of an eye of a subject, during impact of and end of the probe body with the corneal outer surface, when completely stopped on the eye, and during rebound movement of the probe body in a second direction, opposite to the first direction, wherein the computer program causes the computer to calculate an intraocular pressure of the eye as a slope in the time-velocity curve between a time when the end of the probe body first impacts the corneal outer surface and the time when the probe body is completely stopped on the eye, and causes the computer to calculate a central cornea thickness using a velocity of the probe body in the time-velocity curve at a moment of contact of the end of the probe body with the corneal outer surface, Vr, and a velocity of the probe body in the time-velocity curve at the moment when the probe body leaves the corneal outer surface during rebound movement of the probe body in the second direction, Vb.

The computer implemented method or computer program may calculate the central cornea thickness from:

$$D=C\cdot\exp(\tau)+L$$

wherein C and L are constants and $$\tau=(V_r^2-V_b^2)(1-\exp(-K\log p))/V_r^2$$

wherein K is a constant.

C, L and K are constants and may be obtained from a time-velocity curve obtained using an artificial eye model with adjustable intraocular pressure and different thicknesses of the central cornea. Alternatively, the constant can be obtained from a time-velocity curve of an eye of a recently deceased animal, such as a cow, by applying pressure through suction or injection of fluid into the eye as well as creating different cornea thicknesses through cutting of the cornea. Three reference set-ups may be used to obtain values for C, L and K, such as a cornea thickness of 30 μm and an intraocular pressure of 10, 20 and 30 mmHg; a cornea thickness of 530 μm and an intraocular pressure of 10, 20 and 30 mmHg; and a cornea thickness of 1500 μm and an intraocular pressure of 10, 20 and 30 mmHg.

The computer program may further comprise instructions causing the computer to calculate a corrected intraocular pressure using the calculated cornea thickness and the intraocular pressure.

The computer implemented method may further comprise calculating a corrected intraocular pressure using the calculated cornea thickness and the intraocular pressure.

Corrected intraocular pressure is a parameter that is used to unify the effects of central corneal thickness on intraocular pressure. Corrected intraocular pressure is more accurate and more important than the uncorrected alternative. Usually measurement of corrected intraocular pressure requires expensive and sophisticated equipment. With current technology, corneal thickness and uncorrected intraocular pressure are calculated from the very same time-velocity curve and thereafter the corrected pressure may be calculated using the calculated parameters. Thereby, the present computer-implemented method and computer program present a simplified, faster and more cost-effective way of obtaining the corrected intraocular pressure.

By rebuilding and simulating a new curve (velocity, time) based on the calculated cornea thickness and intraocular pressure, using a sophisticated algorithm and geometric equations, the corrected intraocular pressure may be obtained from the new curve.

The computer program may further comprise instructions causing the computer to calculate a tear film thickness on the corneal outer surface from the time-velocity curve, wherein the tear film thickness, L, is calculated from:

$$L=\int_{T_c}^{T_t}V(t)dt$$

V(t) is the velocity-time profile of the probe body registered during the bound and rebound path of the probe body from a time when the end of the probe body hits the eye, completely stops on the eye and until the probe body leaves the eye. $(T_t, V_t)$ is a point in time when the end of the probe body (first impacts the tear film on the corneal outer surface, and $(T_c, V_c)$ is a point in time when the end of the probe body first impacts the corneal outer surface.

The computer implemented method may further comprising calculating a tear film thickness on the corneal outer surface from the time-velocity curve, wherein the tear film thickness, L, is calculated from:

$$L=\int_{T_c}^{T_t}V(t)dt$$

V(t) is the velocity-time profile of the probe body registered during the bound and rebound path of the probe body from a time when the end of the probe body hits the eye, completely stops on the eye and until the probe body leaves the eye, $(T_t, V_t)$ is a point in time when the end of the probe body first impacts the tear film on the corneal outer surface, and $(T_c, V_c)$ is a point in time when the end of the probe body first impacts the corneal outer surface.

In healthy eyes, the cornea is covered by a thin layer of a viscous liquid, a tear film, which may be approximately 5 µm. The tear film creates an interface between the ocular surface and the surrounding environment. If the thickness of the tear film is not sufficiently thick, there is a condition called dry eye disease. Symptoms thereof may range from mild eye burning and itching to corneal perforation in severe cases.

With the above described computer implemented method and computer program it is possible to calculate the tear thickness layer, the cornea thickness, the intraocular pressure and the corrected intraocular pressure, using the very same time-velocity curve.

According to third aspect there is provided a system for determining ophthalmic parameters of a subject, the system comprising a probe and a processor, wherein the processor is arranged to register velocity and time of a probe body of the probe during movement of the probe body in a first direction travelling towards a corneal outer surface of an eye of a subject, during impact of an end of the probe body with the corneal outer surface, when completely stopped on the eye, and during rebound movement of the probe body in a second direction, opposite to the first direction, and the processor further is arranged to, based on a curve obtained from the registered velocity and time of the probe body, calculate an intraocular pressure of the eye as a slope between a time when the end of the probe body first impacts the corneal outer surface and the time when the probe body is completely stopped on the eye, and to, based on the time-velocity curve, calculate a central cornea thickness using a velocity of the probe body at a moment of contact of the end of the probe body with the corneal outer surface, $V_r$, and a velocity of the probe body at the moment when the end of the probe body leaves the corneal outer surface during rebound movement of the probe body in the second direction, $V_b$.

The probe is arranged such that an end of the probe body is at a distance from the corneal outer surface before the probe body is moved in the first direction towards the central area of the corneal outer surface. Such a distance may for example be 3-8 mm.

The end of the probe body may impact the corneal outer surface in a direction substantially vertically to the corneal outer surface and the pupil. This means that the direction is strictly vertical or may deviate from strictly vertical with up to up to ±2.5°.

The cornea thickness measurement may be considered reliable if performed at the vicinity of 1 mm from the centre of the cornea. Outside of this circle, the measured thickness may not be indicative of corneal central thickness.

In the system described above the probe may comprise a magnetic probe body, the probe body having a first and an opposing second end, and a non-magnetic tube having a first and an opposing second end, wherein the magnetic probe body is slidably arranged in the non-magnetic tube, the first end of the probe body and the first end of the tube being oriented in the same direction. A magnetic field being arranged for moving the probe body in a first direction from a first position in the tube to a second position, in which second position at least the first end of the probe body extends out of the first end of the tube, wherein the first end of the probe body may be arranged to, in the second position, to impact a corneal outer surface of an eye of a subject.

The system may further comprise an optical unit arranged at the second end of the non-magnetic tube, co-centred and aligned with the tube, arranged such that light emitted from the optical unit is passed through the non-magnetic tube towards and past the first end of the non-magnetic tube and towards a corneal outer surface vertically arranged at a distance from the first end of the tube, such that the light thereby is reflected from the corneal outer surface and indicates an area on the corneal outer surface of a coming impact of the first end of the probe on the corneal outer surface.

The optical unit may be used to control a position of impact of the end of probe body on the corneal outer surface by, before moving the probe body towards the corneal outer surface, emitting light in a direction towards the corneal outer surface, a direction in which the probe body will move when moved towards the corneal outer surface, light thereby reflected from the corneal outer surface indicating an area on the corneal outer surface of a coming impact of the end of the probe body on the corneal outer surface. Optionally, the position of the coming impact of the end of the probe body on the corneal outer surface may be adjusted by adjusting the position of the probe body relative the corneal outer surface based on the by light indicated position on the corneal outer surface.

A cylindrical and co-centred optical path aligned with the path of the probe body may be used to emit the light. The emitted light, for example by using a LED light source, may create a circular light with a diameter of about 2.6 mm at the corneal surface, indicating an area within which the probe body will impact the corneal outer surface.

Thereby, it may be ensured that the area of the cornea surface impacted by the end of the probe body is a central area of the cornea.

If the light reflected indicates that the surface of a coming impact of the end of the probe body on the corneal outer surface already is in a central portion of the corneal outer surface, no adjustment is needed.

The light emitted may be synchronous light.

The optical unit may be arranged inside the non-magnetic tube.

The system described above may further comprising a display for displaying calculated ophthalmic parameters.

The displayed ophthalmic parameters may be one or more of intraocular pressure, central cornea thickness, corrected corneal pressure, and tear film thickness.

According to a fourth aspect, there is provided a method of determining ophthalmic parameters in a subject, comprising providing a probe body having a first and an opposing second end, arranging the probe body such that an end of the probe body is at a distance from a corneal outer surface of an eye of the subject, moving the probe body in a first direction towards a central area of the corneal outer surface such that the end of the probe body impacts the corneal outer surface and until it is completely stopped on the eye, registering speed and time of the probe body during a bound path of the probe body when the probe body is moved in the first direction, during impact with the corneal outer surface and until the probe body is completely stopped on the eye, and during a rebound path of the probe body when the probe body moves from a complete stop on the eye in a second direction, opposite to the first direction, until the probe body leaves the eye. Based on a curve obtained from the registered velocity and time of the probe, calculate an intraocular pressure of the eye as a slope between a time when the end of the probe body first impacts the corneal outer surface and the time when the probe body is completely stopped on the eye, and to, based on said time-velocity curve, calculate a central cornea thickness using a velocity of the probe body at a moment of contact of the end of the probe body with the corneal outer surface, $V_r$, and a velocity of the probe body at the moment when the end of the probe body leaves the corneal outer surface during rebound of the probe body in the second direction, $V_b$.

The method may also comprise to, based on the calculated intraocular pressure and the corneal thickness, calculate a corrected intraocular pressure.

The method may be performed using the system described above.

DETAILED DESCRIPTION

The thickness of the central part of the cornea, Central Corneal Thickness (CCT), is the most important factor in corneal stability and is on average 530±10 μm in humans, and varies from 300 to 1500 μm in animals, depending on the type of animal. This thickness value is employed by ophthalmologists, not only in the clinical routines as a diagnostic parameter for diseases like glaucoma, but also as a procedural pre-operatory parameter for surgical operations, such as refractive surgeries and corneal transplantation.

In healthy eyes, the cornea is covered by a thin layer of a viscous liquid, a tear film, approximately 5 μm. The tear film creates an interface between the ocular surface and the surrounding environment. If the thickness of the tear film is thinner, there is a condition called dry eye disease. Symptoms thereof may range from mild eye burning and itching to corneal perforation in severe cases.

Intraocular pressure of the eye is the pressure created by the continual renewal of fluids within the eye, which is increased at the presence of diseases such as glaucoma.

Accurate measurement of intraocular pressure helps to improve the diagnosis of glaucoma patients. The intraocular pressure may be defined in two ways: a) as an uncorrected or b) as a corrected pressure.

The uncorrected pressure is measured without taking into account the actual thickness of the cornea and thereby fail to provide sufficient accuracy, especially when measuring on an eye that has previously undergone refractive surgery and therefore has a thinner cornea than normal.

Corrected intraocular pressure is a parameter that is used to unify the effects of central corneal thickness on intraocular pressure. Corrected intraocular pressure is more accurate and more important than the uncorrected alternative, and traditionally requires more expensive and sophisticated equipment. With current technology, corneal thickness and uncorrected intraocular pressure are measured independently and thereafter the corrected pressure may be calculated using the measured parameters.

Below is described a computer-implemented method, a computer program, a system 1 and a method for calculating ophthalmic parameters, including corneal thickness, tear film thickness, uncorrected ophthalmic pressure and corrected ophthalmic pressure from the very same time-velocity curve.

Figure 1:
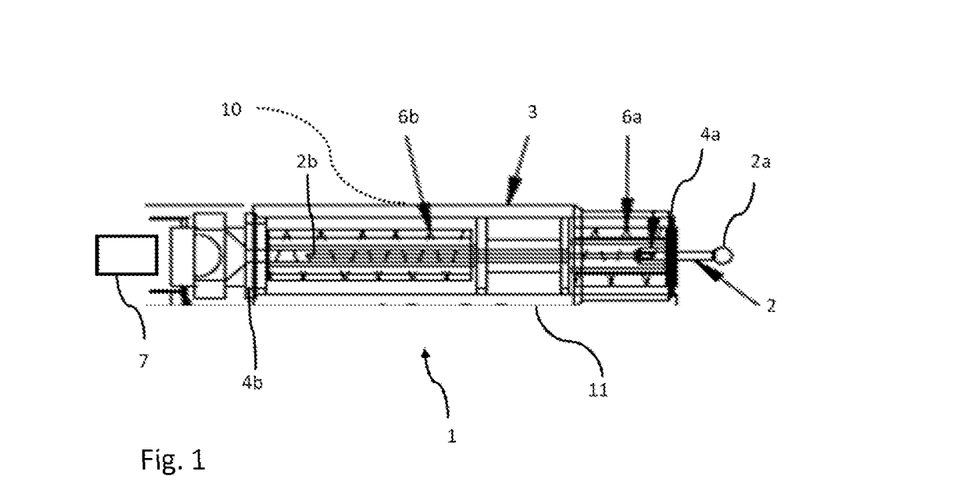
FIG. 1 shows a system comprising a magnetic probe body arranged to move in a magnetic field. The device being used for measuring ophthalmic parameters of an eye of a patient based on registered speed and time of the probe body during movement of the probe body during impact with the corneal outer surface of the eye (bound phase) and during rebound of the probe.
Figure 2:
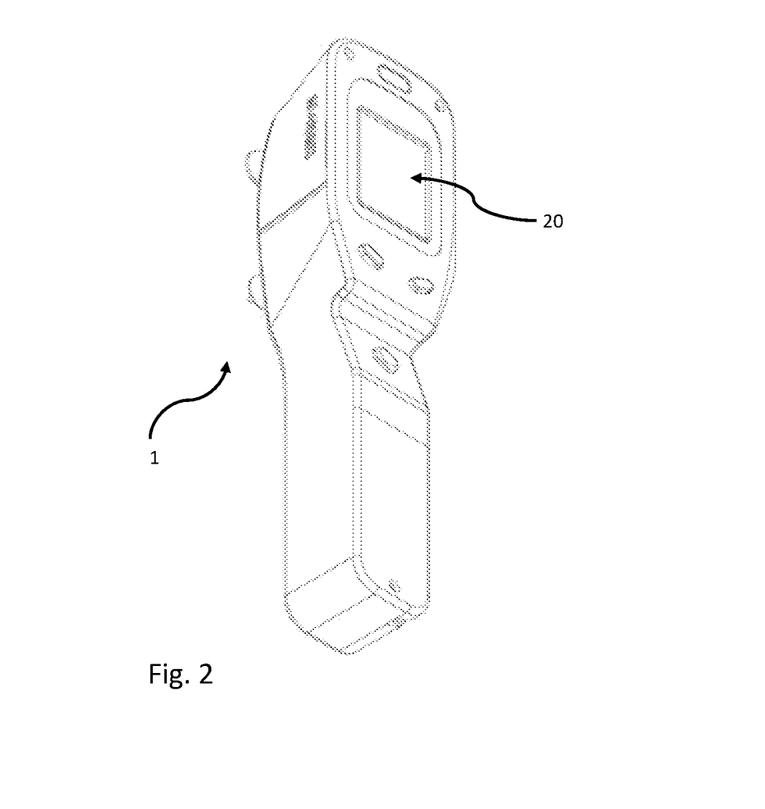
FIG. 2 shows the system of FIG. 1 arranged in a casing.
Figure 4:
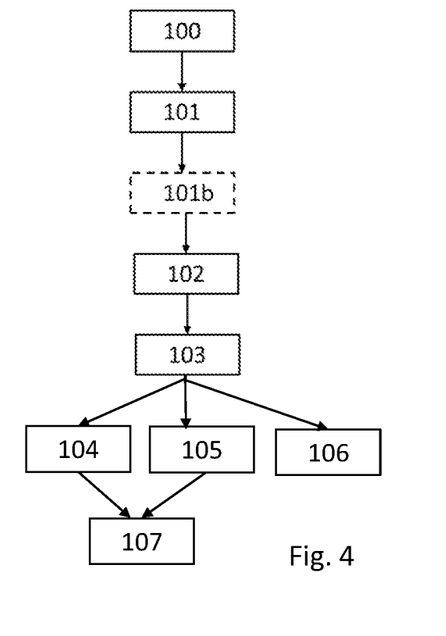
FIG. 4 schematically illustrates a method for measuring ophthalmic parameters in a subject.

In FIG. 1 is illustrated a non-invasive system 1 comprising a magnetic probe 2 arranged to be moved in a magnetic field. The system may be used for measuring ophthalmic parameters of an eye of a human or animal patient. In FIG. 2 is shown the system of FIG. 1 arranged in a casing and with a display 20 for displaying calculated ophthalmic parameters. In FIG. 4 is schematically illustrated a method of measuring ophthalmic parameters with the system.

The system 1 comprises a magnetic probe 2 having a first 2a and an opposing second end 2b. The probe may be arranged in a non-magnetic tube 4 having a first 4a and an opposing second end 4b. The magnetic probe 2 may be slidably arranged in the non-magnetic tube, the first end 2a of the probe and the first end of the tube 4a being oriented in the same direction. The probe 2 is arranged to move in a magnetic field. The magnetic field may be provided by a set of coils 6a, 6b.

As illustrated in FIG. 1, by means of the magnetic field, the probe 2 may be accelerated in a first direction in the tube 4 such that the first end 2a of the probe 2 is caused to extend out from the first end 4a of the tube 4. The first coil 6a may be activated by feeding a voltage to the coil such that the probe is pushed in the first direction.

Having provided 100 the probe body 2 and arranged 101 the probe 2 such that a first end 2a of the probe 2 is at a distance from a corneal outer surface of an eye of the subject, the probe 2 may be moved 102 by means of the magnetic field in the first direction towards a central area of the corneal outer surface such that the first end 2a impacts the corneal outer surface in a direction vertically to the corneal outer surface and until it is completely stopped on the eye, a bound path of the probe body 2. The probe body 2 provided 100 may be arranged 101 such that a first end 2a of the probe 2 is at a distance, such as 3-8 mm, from a corneal outer surface of the eye of the subject.

Upon contact with the corneal outer surface of the eye, the probe body 2 starts to decelerate and rebounds from the eye. As a result, a voltage, which is dependent on the intraocular pressure, is induced in the second coil 6b. This voltage and speed of the probe body 2 may be detected by a second coil 6b and registered 103 by a processor 5. The waveform of the registered amplified signal (speed-time), resulting from the output of the second coil 6b is illustrated in the graph in FIG. 3. In position a) the probe body 2 hits the tear film covering the corneal outer surface; in position b) the probe body hits the corneal outer surface; in position c) the probe body stops at the eye; in position d) the probe body leaves the eye (i.e. the first end 2a of the probe 2 is retracted from the corneal outer surface, because there is no uniform tear film in the rebound path of the probe body 2).

Figure 3:
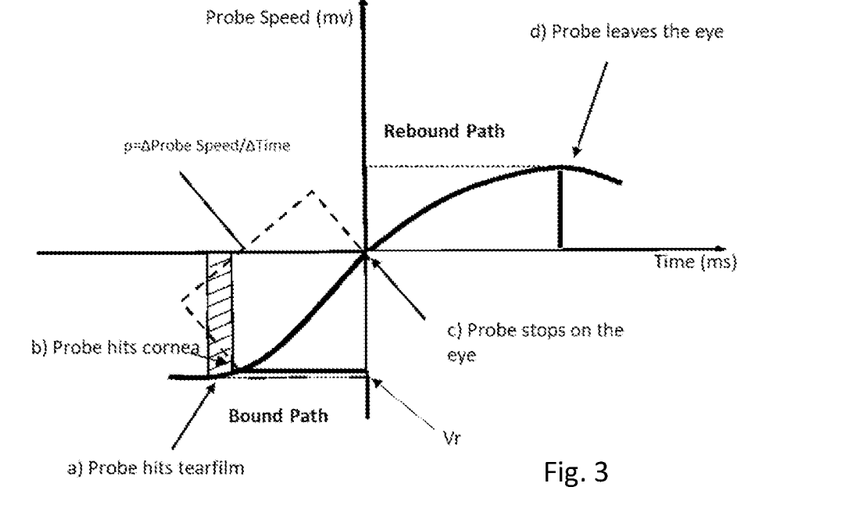
FIG. 3 shows a graph of speed versus time of the probe body of the system shown in FIG. 1 at different positions in the eye: a) the probe body hits the tear film covering the corneal outer surface; b) the probe body hits the corneal outer surface; c) the probe body stops at the eye, d) the probe body leaves the eye.

A computer program may be used, which comprises instructions which, when the program is executed by a computer may cause a computer to carry out analysis of a time-velocity curve, such as the curve illustrated in FIG. 3.

The time-velocity curve may be registered using the system described above, or it may be registered using another system giving the same kind of speed-velocity curve.

The computer program may cause the computer to calculate an intraocular pressure, p, of the eye as a slope in the time-velocity curve between a time when the end of the probe body 2 first impacts the corneal outer surface b and the time when the probe body 2 is completely stopped on the eye, c, and may cause the computer to calculate a central cornea thickness, D, using a velocity of the probe body 2 in the time-velocity curve at a moment of contact of the end 2*a* of the probe body 2 with the corneal outer surface b, $V_r$, and a velocity of the probe body 2 in the time-velocity curve at the moment when the probe body 2 leaves the corneal outer surface during rebound movement of the probe body 2 in the second direction, $V_b$.

The computer program may be used by the processor 5. The calculations performed by the computer program may be displayed on the display 20.

A computer-implemented method may be used for analysing a time-velocity curve as the one shown in FIG. 3. The time-velocity curve may be registered using the system described above, or it may be registered using another system giving the same kind of speed-velocity curve. The computer-implemented method may comprise to calculate an intraocular pressure, p, of the eye as a slope in the time-velocity curve between a time when the end of the probe body 2 first impacts the corneal outer surface b and the time when the probe body 2 is completely stopped on the eye, c, and calculating a central cornea thickness, D, using a velocity of the probe body 2 in the time-velocity curve at a moment of contact of the end 2*a* of the probe body 2 with the corneal outer surface, b, $V_r$, and a velocity of the probe body 2 in the time-velocity curve at a moment when the probe body 2 leaves the corneal outer surface during rebound movement of the probe body 2 in the second direction, $V_b$. The computer-implemented method may be used by the processor 5. The calculations performed in the computer-implemented method may be displayed on the display 20. The time-velocity curve may be registered using the system described above, or it may be registered using another system giving the same kind of speed-velocity curve.

The central cornea thickness, D, may for example be calculated 105 from:

D=C·exp(τ)+L, wherein C and L are constants and τ=$(V_r^2-V_b^2)(1-\exp(-K \log \rho))/V_r^2$, wherein K is a constant, $V_r$ is a velocity of the probe 2 at the moment of contact of the first end 2*a* of the probe 2 with the corneal outer surface, b, in the bound path of the probe body 2, $V_b$ is the velocity of the probe body 2 at the moment when the first end 2*a* of the probe body 2 leaves the corneal outer surface in the rebound path of the probe body 2.

The intraocular pressure obtained above is the so called uncorrected intraocular pressure obtained without taking into account the actual thickness of the cornea. When calculating this pressure, the slope may be measured as an average slope, $$p = \frac{\Delta \text{ Probe Speed}}{\Delta \text{ Time}},$$

and is marked in FIG. 3. The pressure may be calculated using three points on the slope. To eliminate the effects of the tear layer on the eye, the initial points of the curve after the impact with the corneal outer surface may be left out from the slope calculation.

The area below the curve in the bound path is the amount of longitudinal movement of the probe body inward to the eye. The area under the curve in the rebound path is equal to the area under the bound path. Intraocular pressure is inversely related to the amount of longitudinal movement of the probe body in the bound or rebound path, see FIG. 3.

The probe body 2 may be an iron rod with magnetic properties and may be equipped with a plastic cap (probe tip) at its first end 2*a*. At the non-magnetic tube 4, which may be in the form of a pulley cylinder, there are the two coils 6*a*, 6*b*. If each coil is excited by an electric pulse, a relatively strong magnetic field is created inside the non-magnetic tube 4, which causes the probe body 2 to move in the tube 4. The non-magnetic tube 4 may be of aluminium.

Cornea thickness has a very direct logical relationship with the rate of the mechanical energy losses of the probe body 2 after hitting the corneal outer surface. Energy losses are obtained by calculating the difference between the rate of compression at the moment of contact with the eye and the rate of acceleration at the moment when the compression of the eye leaves.

A small amount of these kinetic energy losses (less than 10%) is caused by viscoelastic fluid (gelatinous liquid) inside the eye, which causes the formation of intraocular pressure, and the amount of energy loss due to the gelatinous fluid inside the eye is equal to the amount of pressure. The lower the pressure in the eye, the higher the loss is, and the higher the pressure, the lower the loss is. The compression velocity at the moment of contact with the eye is $V_r$ and the probe body velocity at the moment of leaving the eye $V_b$.

Compressive kinetic energy at both moments, $E_r$ is compressive kinetic energy at collision, $E_b$ is the kinetic energy of the probe body, is the kinetic energy of the probe body when leaving the eye, as well as energy loss and cornea thickness from the following equation:

$$E_r=0.5 \ mV_r^2, \text{ and } E_b=0.5 \ mV_b^2, \text{ and } E_{tp}=(E_r-E_b)=0.5 \ m(V_b^2-V_r^2)$$

$E_{tp}$ has the total amount of energy loss related to cornea thickness (which is above 90% of the total loss) and intraocular pressure (gelatinous fluid inside the eye which is less than 10% of total energy loss), and Ep the rate of energy loss by intraocular pressure and $E_t$ is the amount of energy loss by the cornea, and m is the mass of the mass. Therefore, the amount of energy loss by cornea is obtained from the following equation.

$$E_t=E_{tp}(1-\exp(-K(\log \rho))$$

where K is a constant number and ρ is the intraocular pressure and exp is the mathematical exponential function and log is the logarithmic mathematical function and Et is the energy loss by cornea and $E_{tp}$ is the total energy loss by cornea and intraocular pressure. The eye and the amount of $E_t/E_r$ indicate the thickness of the cornea, and the amount of thickness of the cornea is a correlation with the amount of energy loss by the cornea.

$$\tau = \frac{E_t}{E_r} = \frac{0.5 \ m(V_r^2-V_b^2)(1-\exp(-K\log p))}{0.5 \ m \ V_r^2} = \frac{(V_r^2-V_b^2)(1-\exp(-K\log p))}{V_r^2}$$

The constants C and L may be obtained during a pre-calibration procedure of the device, in order to be able to measure a wide range of the cornea thicknesses, typically spanning from 100 micro meter to 1500 micro meter. In a system setting C and L can for example take value of 781 and −805, respectively.

In one example described above the central cornea thickness, D, was calculated to 530 micro meters, using parameters and constants having values being $V_r=2$ m/s, $V_b=1.6$ m/s, K=3, ρ=7 mmHg, C=781 and L=−805.

The method may further comprise controlling 101b a position of impact of the first end 2a on the corneal outer surface, b, by, before moving 102 the probe body 2 towards the corneal outer surface, b, emitting light in a direction towards the corneal outer surface, a direction in which the probe body 2 will move when moved 102 towards the corneal outer surface. Light thereby reflected from the corneal outer surface indicating an area on the corneal outer surface of a coming impact of the first end 2a of the probe 2 on the corneal outer surface. Optionally, there is then an adjustment of the position of the coming impact of the first end 2a of the probe 2 on the corneal outer surface by adjusting the position of the probe 2 relative the corneal outer surface based on the by light indicated position on the corneal outer surface.

To emit the light, an optical unit 7 may be arranged at the second end 4b of the non-magnetic tube 4, arranged such that light emitted from the optical unit 7 is passed through the non-magnetic tube 4 towards and past the first end 4a of the non-magnetic tube 4 and towards a corneal outer surface, b, vertically arranged at a distance from the first end 4a of the tube 4, such that light thereby reflected from the corneal outer surface indicates an area on the corneal outer surface of a coming impact of the first end 2a of the probe body 2 on the corneal outer surface, b. The emitted light is seen by the patient and shows the user of the device the location of the light hitting the surface of the eye. The user finds the central vertical position of the patient's eye in a subjective way using backlight from the patient's eye.

The method may further comprise a step of by means of the processor calculating 106 a tear film thickness, L, on the corneal outer surface, wherein the tear film thickness, L, is obtained from:

$$L=\int_{T_c}^{T_t}V(t)dt$$

V(t) is the time-speed profile of the probe body 2 registered during the bound and rebound path of the probe body 2 from a time when the probe body 2 hits the eye, b, completely stops, c, on the until the probe leaves the eye, d, $(T_t, V_t)$ is a point in time when the outer tip of the first end 2a of the probe body 2 first impacts the tear film, a, on the corneal outer surface. $(T_c, V_c)$ is a point in time when the first end 2a of the probe body 2 first impacts the corneal outer surface b.

The lacrimal layer, tear layer, is an intermediate fluid between the cornea and the air and it is of a different material (fluid) than the cornea (solid) and air (gas). It has a different stopping coefficient than the compressive motion and the compressive stopping coefficient in the cornea layer. If the compression coefficient in the cornea is $\epsilon_c$, and the compression coefficient in the tear layer is $\epsilon_t$, and the compression coefficient in the air is $\epsilon_\alpha$:

$$\epsilon_\alpha<\epsilon_t<\epsilon_c$$

As a result, we will have the acceleration of the compression stop or the same slope of the velocity-time curve resulting from the winding The return in the graph shown in FIG. 3 will be as follows: Slope is the compression acceleration.

$$Slope_\alpha<Slope_t<Slope_c$$

As a result, by recognizing the point of compression of the compression from the air to the first point of the tear or eye layer $(T_t, V_t)$ and then the point of compression of the compression with the cornea $(T_c, V_c)$, the amount of compression distance in these two points or the thickness of the tear layer obtained:

$$L=\int_{T_c}^{T_t}V(t)dt$$

where L is the thickness of the tear layer and V(t) is the velocity-time curve resulting from the return of the probe 2, FIG. 3 and t is the unit of time.

A corrected intraocular pressure, PC, may be calculated 107 based on/using the calculated cornea thickness, D, and the intraocular pressure, p. This may be done in the following way and is illustrated in the graphs shown in FIGS. 5 and 6.

Figure 5:
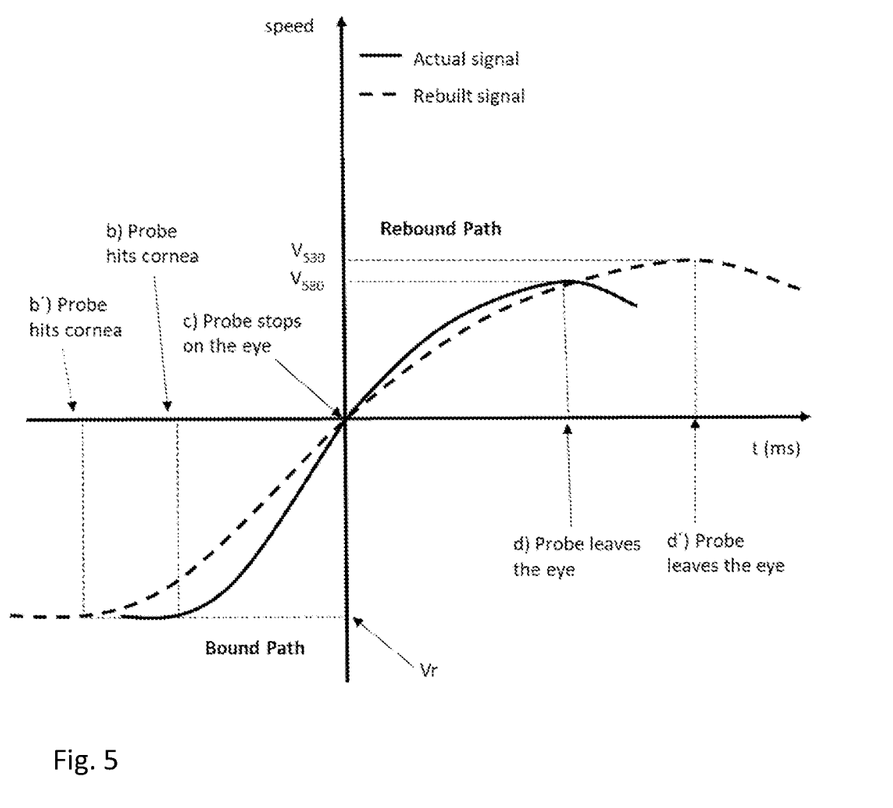
FIGS. 5 and 6 show the same kind of graph as illustrated in FIG. 3, and reconstructed graphs (dashed lines), which are reconstructed using a respective cornea thickness value and intraocular pressure calculated from the original graphs (solid lines). The reconstructed graph being used to calculate a corrected intraocular pressure.

In FIG. 5 is shown the registered speed and time of the probe body 2 during the bound path of the probe during movement of the probe body in the first direction, during impact with the corneal outer surface, when completely stopped on the eye, and during the rebound path of the probe body 2 in a second direction opposite to the first direction, is shown as a solid line. In this example, the cornea thickness obtained from this signal was 580 μm and the intraocular pressure calculated was 20 mmHg.

This measured signal can then be reconstructed for a "normal" cornea thickness of 530 μm (on average the corneal thickness of humans is 530±10 μm) and an intraocular pressure of <20 mmHg. A pressure of <20 mmHg being used as the thicker cornea measured, 580 μm, causes a higher pressure measurement in the device.

The measured signal can be reconstructed into the reconstructed signal (dashed line in FIG. 5) in the following way:
1) $V_b$ for the corneal thickness of 530 micron is obtained from the equation of τ (see above).
2) $V_r$ is the same as $V_r$ obtained for the measured signal.
3) The slope rate of the rebound path of the probe body 2 is obtained from the measured and reconstructed value of $V_b$ and time.
4) The amount of velocities over time in the rebound path of the probe body is calculated based on the slope rate and actual signal, point to point.
5) The area under the reconstructed curve in the rebound path of the probe body is calculated. (The amount of probe depression in the eye surface).
6) The amount of depression, in the bound phase is the same as in the rebound phase.
7) The rate of slope rate in the bound phase to slope rate in the rebound phase is calculated in the actual measured signal (corneal biomechanical property) and should be the same in the reconstructed signal. Then the slope rate in the bound phase is calculated.
8) The velocity-time curve is reconstructed for the bound phase based on the slope rate in the bound phase and the signal depression.
9) Calculating the corrected intraocular pressure using the reconstructed curve.

The corrected intraocular pressure, CP, may then be calculated from the reconstructed curve as a slope, indicated in FIG. 5 between a time when the first end 2a of the probe body 2 first impacts the corneal outer surface, b', and the time when the probe body 2 is completely stopped on the eye, c.

Figure 6:
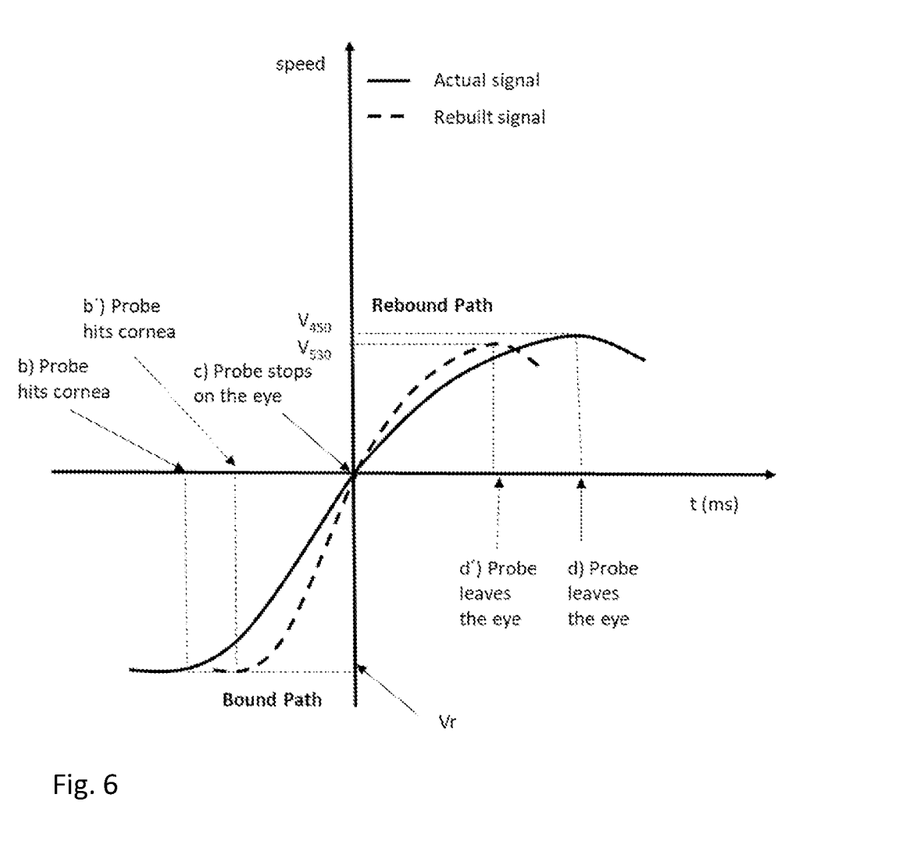

In FIG. 6 is shown an example in which the cornea thickness obtained from the registered speed-time signal was 450 µm and the intraocular pressure calculated was 20 mmHg. This signal was reconstructed, shown as a dashed line in FIG. 6, based on a cornea thickness of 530 µm and an intraocular pressure of >20 mmHg (as the thin cornea causes a lower pressure measurement in the device. The CP is then calculated from the reconstructed curve as a slope, indicated in FIG. 6 between a time when the first end 2a of the probe 2 first impacts the corneal outer surface, b', and the time when the probe body 2 is completely stopped on the eye, c.

To increase the accuracy of the calculations, the calculated parameters may be average values from of a plurality, such as 2-4, of measurements or time-velocity curves, The system may be used without the need for anaesthetic drops.

The first coil 6a may be activated for about 10 ms, and the magnetic field created causes the probe body 2 to move towards the eye with a certain and stable velocity in the first about 10 mm of movement. The amount of velocity is monitored by the second coil 6b. The end 2a of the probe body 2 hits the tear film and thereafter the outer surface of the cornea. The probe body will compress the cornea until it is completely stopped on the cornea surface (bound phase). Thereafter the intraocular pressure of the eye causes the reverse movement of the probe body until completely leaving the eye (rebound phase). The velocity profile during the bound and rebound phase is registered in the system. When the processor detects that the probe body 2 has left the eye, the second coil 6b is activated (in about 100 ms) in order to bring the probe back into its starting position.

The total time of for the bound and rebound phase fora target with an uncorrected intraocular pressure of 70 mmHg is around 1 ms and for a target with an uncorrected intraocular pressure of 7 mmHg it is around 5 ms.

For controlling the velocity of the probe body 2, the first coil and the second coil, 6a and 6b, may be activated sequentially for short intervals such as during 2 ms-3 ms and 4 ms-5 ms, respectively, for several times. If the velocity of the probe body deviates from a specific value, a warning may be shown for example on the display 20 to a user of the system. This process is performed only once for a complete measurement of multiple trials.

The system 1 may be a portable system or a desktop system.

The invention claimed is:

1. A computer-implemented method for analysing a time-velocity curve, the time-velocity-curve comprising registered velocity and time of a probe body (2) during movement of the probe body in a first direction travelling towards a corneal outer surface of an eye of a subject, during impact of an end (2a) of the probe body (2) with the corneal outer surface (b), when completely stopped on the eye (c), and during rebound movement of the probe body (2) in a second direction, opposite to the first direction, the computer-implemented method comprising calculating an intraocular pressure (ρ) of the eye as a slope in the time-velocity curve between a time when the end of the probe body (2) first impacts the corneal outer surface (b) and the time when the probe body (2) is completely stopped on the eye (c), and calculating a central cornea thickness (D) using a velocity of the probe body (2) in the time-velocity curve at a moment of contact of the end (2a) of the probe body (2) with the corneal outer surface (b), $V_r$, and a velocity of the probe body (2) in the time-velocity curve at a moment when the probe body (2) leaves the corneal outer surface during rebound movement of the probe body (2) in the second direction, $V_b$.

2. A non-transitory computer-readable storage medium comprising computer-readable instructions which, when executed:
carry out analysis of a time-velocity curve, the time-velocity curve comprising registered velocity and time of a probe body (2) during movement of the probe body in a first direction travelling towards a corneal outer surface of an eye of a subject, during impact of and end (2a) of the probe body (2) with the corneal outer surface (b), when completely stopped on the eye (c), and during rebound movement of the probe body (2) in a second direction, opposite to the first direction,
calculate an intraocular pressure (ρ) of the eye as a slope in the time-velocity curve between a time when the end of the probe body (2) first impacts the corneal outer surface (b) and the time when the probe body (2) is completely stopped on the eye (c), and
calculate a central cornea thickness (D) using a velocity of the probe body (2) in the time-velocity curve at a moment of contact of the end (2a) of the probe body (2) with the corneal outer surface (b), Vr, and a velocity of the probe body (2) in the time-velocity curve at the moment when the probe body (2) leaves the corneal outer surface during rebound movement of the probe body (2) in the second direction, Vb.

3. The computer implemented method of claim 1 wherein the central cornea thickness (D) is calculated from:

$$D=C \cdot \exp(\tau)+L$$

wherein C and L are constants and $$\tau=(V_r^2-V_b^2)(1-\exp(-K \log \rho))/V_r^2$$

wherein K is a constant.

4. The non-transitory computer-readable storage medium of claim 2, wherein the instructions are further configured to calculate a corrected intraocular pressure (CP) using the calculated cornea thickness (D) and the intraocular pressure (ρ).

5. The computer-implemented method of claim 1, further comprising calculating a corrected intraocular pressure (CP) using the calculated cornea thickness (D) and the intraocular pressure (ρ).

6. The non-transitory computer-readable storage medium of claim 2, wherein the instructions are further configured to calculate a tear film thickness (L) on the corneal outer surface from the time-velocity curve, wherein the tear film thickness (L) is calculated from:

$$L=\int_{T_c}^{T_t} V(t)dt$$

V(t) is the velocity-time profile of the probe body (2) registered during the bound and rebound path of the probe body (2) from a time when the end (2a) of the probe body (2) hits the eye, completely stops on the eye and until the probe body (2) leaves the eye, ($T_t$, $V_t$) is a point in time when the end (2a) of the probe body (2) first impacts the tear film (a) on the corneal outer surface, ($T_c$, $V_c$) is a point in time when the end (2a) of the probe body (2) first impacts the corneal outer surface (b).

7. The computer implemented method of claim 1, further comprising calculating a tear film thickness (L) on the corneal outer surface from the time-velocity curve, wherein the tear film thickness (L) is calculated from:

$$L=\int_{T_c}^{T_t} V(t)dt$$

V(t) is the velocity-time profile of the probe body (2) registered during the bound and rebound path of the probe body (2) from a time when the end (2a) of the probe body (2) hits the eye, completely stops on the eye and until the probe body (2) leaves the eye, ($T_t$, $V_t$) is a point in time when the end (2a) of the probe body (2) first impacts the tear film (a) on the corneal outer surface, ($T_c$, $V_c$) is a point in time when the end (2a) of the probe body (2) first impacts the corneal outer surface (b).

8. A system (1) for determining ophthalmic parameters of a subject, the system comprising a probe (11) and a processor (10), wherein the processor is arranged to register velocity and time of a probe body (2) of the probe (11) during movement of the probe body in a first direction travelling towards a corneal outer surface of an eye of a subject, during impact of an end (2a) of the probe body (2) with the corneal outer surface (b), when completely stopped on the eye (c), and during rebound movement of the probe body (2) in a second direction, opposite to the first direction, and the processor (10) further is arranged to, based on a curve obtained from the registered velocity and time of the probe body (2), calculate an intraocular pressure (ρ) of the eye as a slope between a time when the end (2a) of the probe body (2) first impacts the corneal outer surface (b) and the time when the probe body (2) is completely stopped on the eye (c), and to, based on said time-velocity curve, calculate a central cornea thickness (D) using a velocity of the probe body (2) at a moment of contact of the end (2a) of the probe body (2) with the corneal outer surface (b), $V_r$, and a velocity of the probe body (2) at the moment when the end (2a) of the probe body (2) leaves the corneal outer surface during rebound movement of the probe body (2) in the second direction, $V_b$.

9. The system (1) of claim 8, wherein the probe (2) comprises:

a magnetic probe body (2), the probe body (2) having a first (2a) and an opposing second end (2b), a non-magnetic tube (4) having a first (4a) and an opposing second end (4b), wherein the magnetic probe body (2) is slidably arranged in the non-magnetic tube (4), the first end (2a) of the probe body (2) and the first end (4a) of the tube (4) being oriented in the same direction, a magnetic field arranged for moving the probe body (2) in a first direction from a first position in the tube to a second position, in which second position at least the first end (2a) of the probe body (2) extends out of the first end (4a) of the tube (4), the first end (2a) of the probe body (2) being arranged to, in said second position, to impact a corneal outer surface (b) of an eye of a subject.

10. The system of claim 8, wherein an optical unit (7) is arranged at the second end (4b) of the non-magnetic tube (4), co-centred and aligned with the tube, arranged such that light emitted from the optical unit (7) is passed through the non-magnetic tube (4) towards and past the first end (4a) of the non-magnetic tube (4) and towards a corneal outer surface (b) vertically arranged at a distance from the first end (4a) of the tube (4), such that the light thereby is reflected from the corneal outer surface indicates an area on the corneal outer surface of a coming impact of the first end (2a) of the probe (2) on the corneal outer surface (b).

11. The system of claim 8, further comprising a display (20) for displaying calculated ophthalmic parameters.

12. Method of determining ophthalmic parameters in a subject, comprising providing (100) a probe body having a first (2a) and an opposing second end (2b), arranging (101) the probe body (2) such that an end (2a) of the probe body (2) is at a distance from a corneal outer surface (b) of an eye of the subject, moving (102) the probe body (2) in a first direction towards a central area of the corneal outer surface (b) such that the end (2a) of the probe body impacts the corneal outer surface (b) and until it is completely stopped on the eye (c), registering (103) speed and time of the probe body (2) during a bound path of the probe body (2) when the probe body (2) is moved in the first direction, during impact with the corneal outer surface (b) and until the probe body (2) is completely stopped on the eye (c), and during a rebound path of the probe body (2) when the probe body (2) moves from a complete stop on the eye (c) in a second direction, opposite to the first direction, until the probe body (2) leaves the eye (d), based on a curve obtained from the registered velocity and time of the probe, calculate (104) an intraocular pressure (ρ) of the eye as a slope between a time when the end (2a) of the probe body (2) first impacts the corneal outer surface (b) and the time when the probe body (2) is completely stopped on the eye (c), and to, based on said time-velocity curve, calculate (105) a central cornea thickness (D) using a velocity of the probe body (2) at a moment of contact of the end of the probe body (2) with the corneal outer surface (b), $V_r$, and a velocity of the probe body (2) at the moment when the end (2a) of the probe body (2) leaves the corneal outer surface during rebound of the probe body (2) in the second direction, $V_b$.

13. The non-transitory computer-readable storage medium of claim 2, wherein the central cornea thickness (D) is calculated from:

$$D = C \cdot \exp(\tau) + L$$

wherein C and L are constants and $$t = (V_r^2 - V_b^2)(1 - \exp(-K \log \rho))/V_r^2$$

wherein K is a constant.

14. The computer implemented method of claim 5, further comprising calculating a tear film thickness (L) on the corneal outer surface from the time-velocity curve, wherein the tear film thickness (L) is calculated from:

$$L = \int_{T_c}^{T_t} V(t) dt$$

V(t) is the velocity-time profile of the probe body (2) registered during the bound and rebound path of the probe body (2) from a time when the end (2a) of the probe body (2) hits the eye, completely stops on the eye and until the probe body (2) leaves the eye, (Tt, Vt) is a point in time when the end (2a) of the probe body (2) first impacts the tear film (a) on the corneal outer surface, (Tc, Vc) is a point in time when the end (2a) of the probe body (2) first impacts the corneal outer surface (b).

15. The system of claim 9, wherein an optical unit (7) is arranged at the second end (4b) of the non-magnetic tube (4), co-centred and aligned with the tube, arranged such that light emitted from the optical unit (7) is passed through the non-magnetic tube (4) towards and past the first end (4a) of the non-magnetic tube (4) and towards a corneal outer surface (b) vertically arranged at a distance from the first end (4a) of the tube (4), such that the light thereby is reflected from the corneal outer surface indicates an area on the corneal outer surface of a coming impact of the first end (2*a*) of the probe (2) on the corneal outer surface (b).

\* \* \* \* \*

UNITED STATES PATENT AND TRADEMARK OFFICE
CERTIFICATE OF CORRECTION

PATENT NO. : 11,925,413 B2
APPLICATION NO. : 18/253277
DATED : March 12, 2024
INVENTOR(S) : Arash Ghareh Baghi et al.

It is certified that error appears in the above-identified patent and that said Letters Patent is hereby corrected as shown below:

In the Claims

In Column 14, Line 11, Claim 2, delete "and end" and insert -- an end --, therefor.

In Column 14, Line 29, Claim 3, delete "computer implemented" and insert -- computer-implemented --, therefor.

In Column 14, Line 32, Claim 3, delete "$D=C \cdot \exp(\tau)+L$" and insert -- $D=C.\exp(\tau)+L$ --, therefor.

In Column 14, Line 62, Claim 7, delete "computer implemented" and insert -- computer-implemented --, therefor.

In Column 15, Line 40, Claim 9, delete "first (4a)" and insert -- first end (4a) --, therefor.

In Column 15, Line 53, Claim 10, delete "system" and insert -- system (1) --, therefor.

In Column 15, Line 64, Claim 11, delete "system" and insert -- system (1) --, therefor.

In Column 16, Line 38, Claim 13, delete "$D=C \cdot \exp(\tau)+L$" and insert -- $D=C.\exp(\tau)+L$ --, therefor.

In Column 16, Line 41, Claim 13, delete "$t=(V_r^2-V_b^2)(1-\exp(-K \log \rho))/V_r^2$" and insert -- $\tau=(V_r^2-V_b^2)(1-\exp(-K \log \rho))/V_r^2$ --, therefor.

In Column 16, Line 43, Claim 14, delete "computer implemented" and insert -- computer-implemented --.

In Column 16, Line 59, Claim 15, delete "system" and insert -- system (1) --, therefor.

Signed and Sealed this
Sixth Day of August, 2024

*Katherine Kelly Vidal*
Katherine Kelly Vidal
*Director of the United States Patent and Trademark Office*